(12) United States Patent
Charles et al.

(10) Patent No.: US 11,033,427 B2
(45) Date of Patent: Jun. 15, 2021

(54) VITREORETINAL INSTRUMENTS FOR FLUID ASPIRATION

(71) Applicant: Novartis AG, Basel (CH)

(72) Inventors: Steven T. Charles, Memphis, TN (US); Reto Grueebler, Greifensee (CH); Philipp Schaller, Stein am Rhein (CH)

(73) Assignee: Alcon Inc., Fribourg (CH)

( * ) Notice: Subject to any disclaimer, the term of this patent is extended or adjusted under 35 U.S.C. 154(b) by 126 days.

(21) Appl. No.: 15/926,302

(22) Filed: Mar. 20, 2018

(65) Prior Publication Data

US 2018/0296391 A1 Oct. 18, 2018

Related U.S. Application Data

(60) Provisional application No. 62/485,154, filed on Apr. 13, 2017.

(51) Int. Cl.
*A61F 9/007* (2006.01)
*A61M 1/00* (2006.01)

(52) U.S. Cl.
CPC ....... *A61F 9/00736* (2013.01); *A61M 1/0045* (2014.02); *A61M 1/0064* (2013.01); *A61M 2205/0266* (2013.01); *A61M 2205/587* (2013.01); *A61M 2210/0612* (2013.01)

(58) Field of Classification Search
CPC ............. A61F 9/00736; A61M 1/0045; A61M 2205/0266; A61M 2210/0612; A61M 2205/587; A61M 1/0064
See application file for complete search history.

(56) References Cited

U.S. PATENT DOCUMENTS

| | | | |
|---|---|---|---|
| 4,395,258 A | 7/1983 | Wang et al. | |
| 4,493,698 A | 1/1985 | Wang et al. | |
| 4,530,356 A | 7/1985 | Helfgott et al. | |
| 6,135,984 A * | 10/2000 | Dishler | A61F 9/007 604/181 |
| 6,364,853 B1 * | 4/2002 | French | A61M 1/0064 137/596.2 |
| 7,141,048 B1 | 11/2006 | Charles | |
| 7,285,107 B1 | 10/2007 | Charles | |
| 9,351,871 B2 | 5/2016 | Ghannoum | |
| 9,433,725 B2 | 9/2016 | Schaller | |
| 9,730,834 B2 | 8/2017 | Charles | |

(Continued)

FOREIGN PATENT DOCUMENTS

WO WO2016159999 A1 10/2016

*Primary Examiner* — Theodore J Stigell
*Assistant Examiner* — Rachel T. Smith

(57) ABSTRACT

Vitreoretinal instruments and methods related thereto are disclosed herein. The disclosure describes various example vitreoretinal instruments having various aspirating port configurations. A vitreoretinal instrument may include a handle and a cannula coupled to the handle. The cannula may include a straight portion and a curved portion. The curved portion may be configurable between a straight configuration and a curved configuration. The curved configuration may include a first curved portion having a curvature defined by a first radius. The curved configuration may include a second curved portion having a curvature defined by a second radius different from the first radius. The curved portion may further include one or more ports formed in the curved portion.

19 Claims, 11 Drawing Sheets

(56) References Cited

U.S. PATENT DOCUMENTS

| | | |
|---|---|---|
| 9,925,088 B2 | 3/2018 | Clem |
| 9,931,173 B2 | 4/2018 | Prisco |
| 9,949,874 B2 | 4/2018 | Contiliano |
| 10,010,447 B2 | 7/2018 | Kashani |
| 10,064,752 B2 | 9/2018 | Price |
| 10,226,379 B2 | 3/2019 | Oberkircher |
| 10,299,958 B2 | 5/2019 | Badawi |
| 10,478,553 B2 | 11/2019 | Meyer |
| 10,507,134 B2 | 12/2019 | Charles |
| 10,555,834 B2 | 2/2020 | Charles |
| 2003/0069549 A1* | 4/2003 | MacMahon ......... A61M 1/0009 604/266 |
| 2009/0131885 A1* | 5/2009 | Akahoshi ............ A61F 9/00736 604/272 |
| 2009/0157002 A1* | 6/2009 | Dumot .............. A61M 25/0029 604/131 |
| 2010/0114093 A1* | 5/2010 | Mahapatra ......... A61B 18/1492 606/41 |
| 2011/0125139 A1 | 5/2011 | Auld |
| 2014/0171997 A1 | 11/2014 | Heck |
| 2015/0173947 A1 | 6/2015 | Charles |
| 2017/0071788 A1 | 3/2017 | Anderson |
| 2017/0172389 A1* | 6/2017 | Fujisaki ............. A61B 1/00154 |
| 2017/0216092 A1* | 8/2017 | Singh .................. A61F 9/00736 |
| 2018/0042768 A1 | 2/2018 | Charles |
| 2019/0105197 A1 | 4/2019 | Labelle |

\* cited by examiner

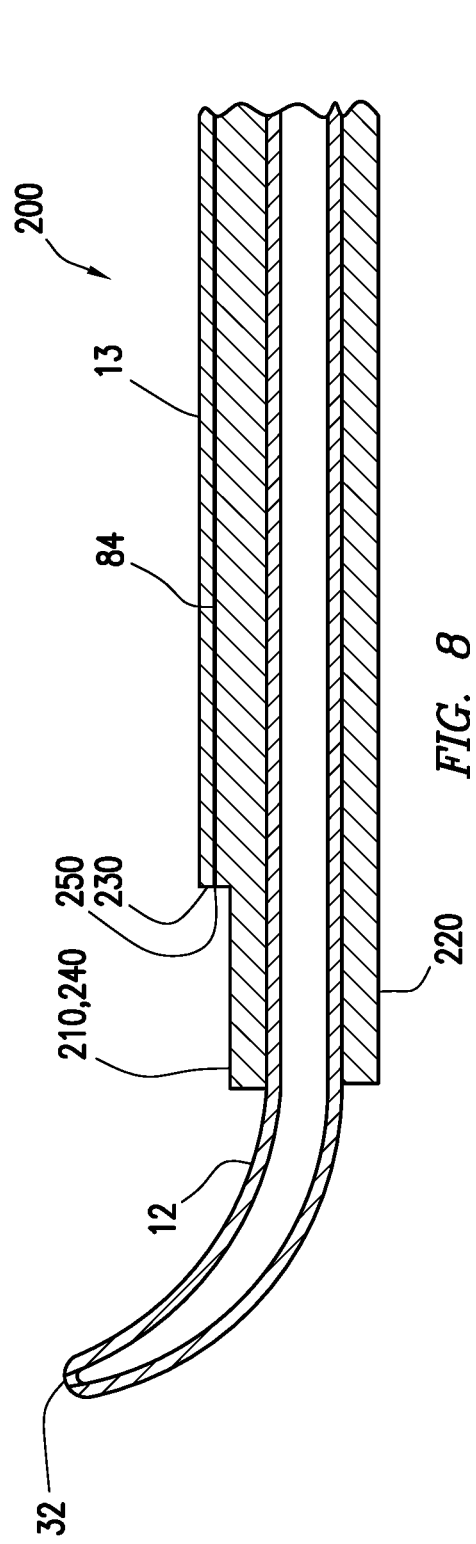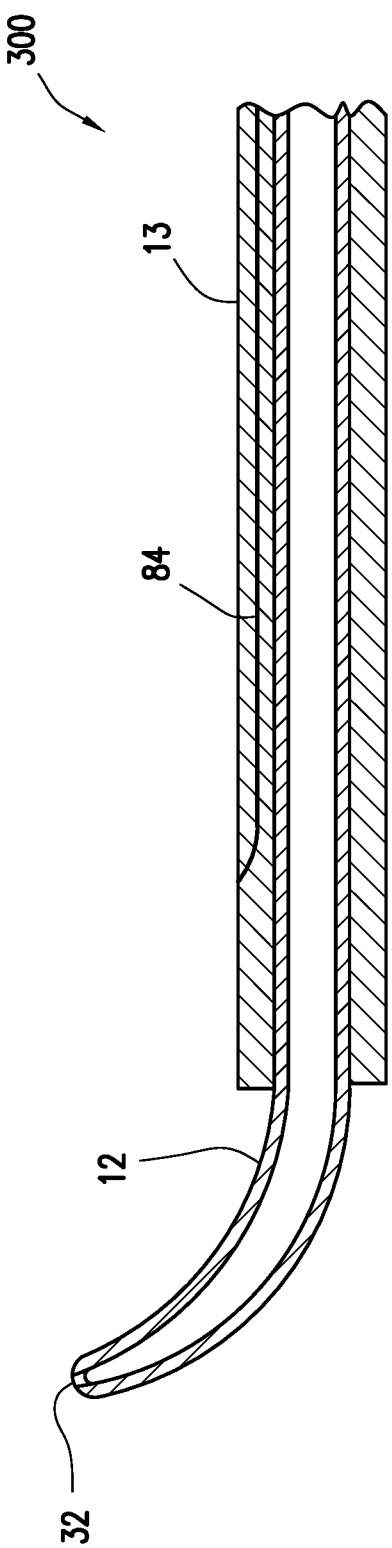

VITREORETINAL INSTRUMENTS FOR FLUID ASPIRATION

BACKGROUND

In a healthy human eye, the retina may be physically attached to the choroid in a generally circumferential manner behind the pars plana. The vitreous humor, a transparent jelly-like material that fills the posterior segment of the eye, may help to cause the remainder of the retina to lie against, but not physically attach, to the choroid.

Sometimes a portion of the retina may become detached from the retinal pigment epithelium ("RPE"). Other times, a portion of the retina may tear, allowing vitreous humor, and sometimes aqueous humor, to flow between the retina and the RPE, creating a build-up of subretinal fluid. Both of these conditions may result in a loss of vision.

To surgically repair these conditions, a surgeon may insert a vitreoretinal instrument into the posterior segment of the eye via a sclerotomy, an incision through the sclera at the pars plana. The surgeon may also insert a fiber optic light source and an infusion cannula into the eye via similar incisions and may sometimes substitute an aspiration probe for the vitreoretinal instrument. While viewing the posterior segment under a microscope and with the aid of the fiber optic light source, the surgeon may cut and aspirate away vitreous using the vitreoretinal instrument to gain access to the retinal detachment or tear. During this portion of the surgery, a saline solution may be infused into the eye via the infusion cannula to maintain the appropriate intraocular pressure.

Next, the surgeon may remove fluid under the retina and inject air, an air-gas mixture, or perfluorocarbon to reapproximate the detached or torn portion of the retina to flatten against the choroid in the proper location. A soft tip cannula, forceps, or pick may be utilized for such manipulation. Many surgeons may also inject perfluorocarbon liquid as a retinal tamponade fluid into the posterior segment of the eye while aspirating the saline solution in the posterior segment to help flatten the detached or torn portion of the retina against the choroid in the proper location. This procedure may be referred to as a "fluid/perfluorocarbon" exchange. Other surgeons may inject air as a retinal tamponade fluid into the posterior segment of the eye while aspirating the saline solution. This procedure may be referred to as a "fluid/air" exchange. Finally, other surgeons may inject a mixture of air and a gas such as $SF_6$, $C_3F_8$, or $C_2F_6$ as a retinal tamponade fluid into the posterior segment of the eye while aspirating the saline solution. This procedure may be referred to as a "fluid/gas" exchange. As used herein, a "fluid" may include any liquid or gas that is suitable for use in the eye, including, but not limited to, saline solution with or without additives, silicone oil, a perfluorocarbon liquid, air, or a perfluorocarbon gas.

After performing one of the above-described exchanges, the surgeon may then drain any sub-retinal fluid present between the retina and the choroid. Instruments presently used to drain subretinal fluid suffer from certain disadvantages. Particularly, as these instruments aspirate sub-retinal fluid, they may often incarcerate the retina into their port. These instruments may also sometimes cause avulsion of portions of the retinal pigment epithelium. Further, these instruments may sometimes cause mechanical damage to the choriocapillaris and choroid, causing bleeding that may further complicate retinal reattachment, and may further obscure the visual field.

SUMMARY

In an exemplary aspect, the present disclosure is directed to a vitreoretinal instrument including a handle and a cannula coupled to the handle. The cannula may include a straight portion, a curved portion, and one or more ports formed in the curved portion. The curved portion may be configurable between a straight configuration and a curved configuration. The curved configuration may include a first curved portion having a curvature defined by a first radius and a second curved portion having a curvature defined by a second radius. In some instances, the second radius may be different from the first radius.

In another exemplary aspect, the present disclosure is directed to a method for operating a vitreoretinal instrument. The method may include providing the vitreoretinal instrument. The vitreoretinal instrument may include a handle and a cannula coupled to the handle. The cannula may include a straight portion, a curved portion and one or more ports formed in the curved portion. The curved portion may be configurable between a straight configuration and a curved configuration. The curved configuration may include a first curved portion having a curvature defined by a first radius and a second curved portion having a curvature defined by a second radius. In some instances, the second radius may be different from the first radius. The method may include positioning the vitreoretinal instrument in a subretinal space of an eye such that the curved portion is at least partially in the subretinal space; and aspirating fluid from the subretinal space through at least the one or more ports.

The different aspects may include one or more of the following features. The one or more ports may include a tip port formed at a distal tip of the curved portion and a plurality of lateral ports that may be formed along a length the curved portion. The plurality of lateral ports may be arranged in two or more rows. The lateral ports may progressively decrease in size with increasing distance from the tip port. At least one of the plurality of lateral ports may be oval in shape. A distal tip of the curved portion may be unperforated. The vitreoretinal instrument may also include an outer tube. The cannula may be extendable and retractable within the outer tube, and a shape of the curved portion may be variable between the curved configuration as the cannula is extended from the outer tube and the straight configuration as the cannula is retracted into the outer tube. The vitreoretinal instrument may also include a mechanism on the handle to extend and retract the cannula from the outer tube. The distal end of the cannula may define a first longitudinal axis, and the straight portion may define a second longitudinal axis. An angle defined between the first longitudinal axis and the second longitudinal axis may be variable in response to extension of the cannula from the outer tube or retraction of the cannula into the outer tube. The one or more ports may include a tip port formed at a distal tip of the curved portion, and the tip port may be beveled or double-beveled. The one or more ports may include a tip port formed in a distal tip of the curved portion, and the tip port may be oriented at an angle offset from a longitudinal axis of a distal end of the curved portion. The second radius may be larger than the first radius, and the second curved portion may be located closer to a distal tip of the curved portion than the first curved portion. The second curved portion conforms in shape with a retinal pigment epithelium layer. The first radius and the second radius may be adjustable. The curved portion may include at least one elastic material selected from the group consisting of a thermoplastic elastomer and a shape memory alloy. The vitreoretinal instrument may include a vacuum source and tubing fluidly coupled to the vacuum source and the one or more ports. The tubing may extend into the handle. The handle may include a compression valve moveable between a first position in which the tubing is placed into an open configuration and a second position in which the tubing is placed into a closed configuration.

The different aspects may include one or more of the following features. A curvature of the curved portion may be adjusted. The vitreoretinal instrument may include an outer tube. The cannula may be extended from the outer tube such that the curved portion of the cannula curves into the curved configuration. The one or more ports may include a tip port formed in a distal tip of the curved portion and a plurality of lateral ports formed along a length of the curved portion. The plurality of lateral ports may be arranged in two or more rows. The lateral ports may progressively decrease in size with increasing distance from the tip port.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

These drawings illustrate examples of certain aspects of some of the embodiments of the present disclosure and should not be used to limit or define the disclosure.

FIG. 8 illustrates another example vitreoretinal instrument that includes an optical fiber whose distal end is located at an end of a groove formed in an outer tube.

FIG. 9 illustrates a further vitreoretinal instrument in which an optical fiber is embedded in an outer tube, the distal end of the optical fiber terminating at the outer surface of the outer tube.

DETAILED DESCRIPTION

Figure 1:
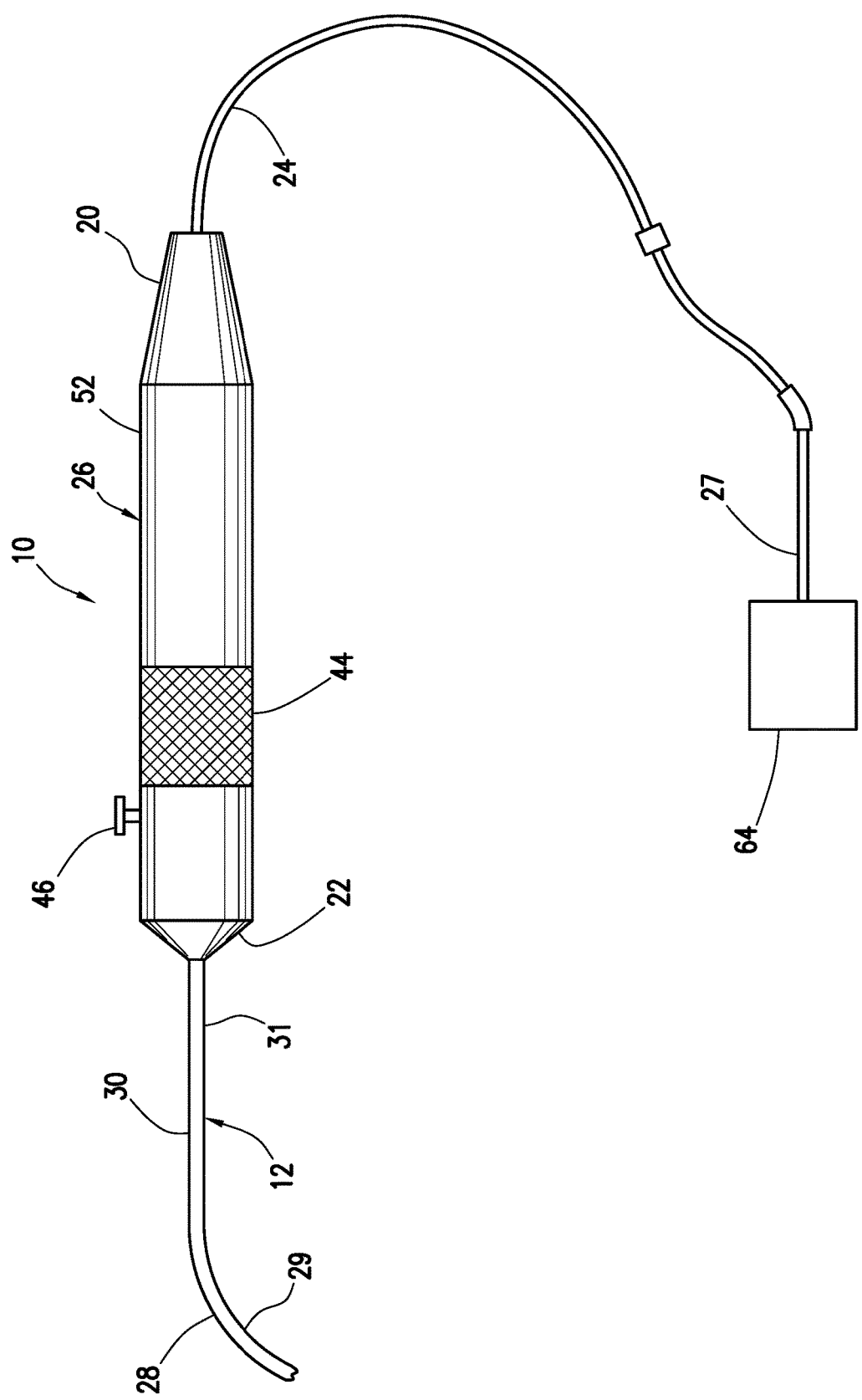
FIG. 1 illustrates an example vitreoretinal instrument.

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

The present disclosure generally relates to vitreoretinal instruments for aspiration of subretinal fluid and associated methods of use. In relation to current vitreoretinal instruments, access to subretinal space without incarceration of the retina may be difficult. Straight vitreoretinal instruments may not be able to access the retinal break/subretinal space, and, as such, straight vitreoretinal instruments may be limited to a location at the boundary of the retinal break, which may result in retinal incarceration.

In accordance with example embodiments described herein, a vitreoretinal instrument's tip port, in combination with lateral ports, may access the subretinal space by adjusting an angle of the vitreoretinal instrument. With the optimized port design, the retina may be less attracted as a result of low suction forces. Further, a cannula of vitreoretinal instruments within the scope of the present disclosure may be retracted for insertion through an incision and extended once in the eye. Based on the length of extension, the angle may be adjusted (between about 90° fully extended, and about 0° almost fully retracted).

Figure 2:
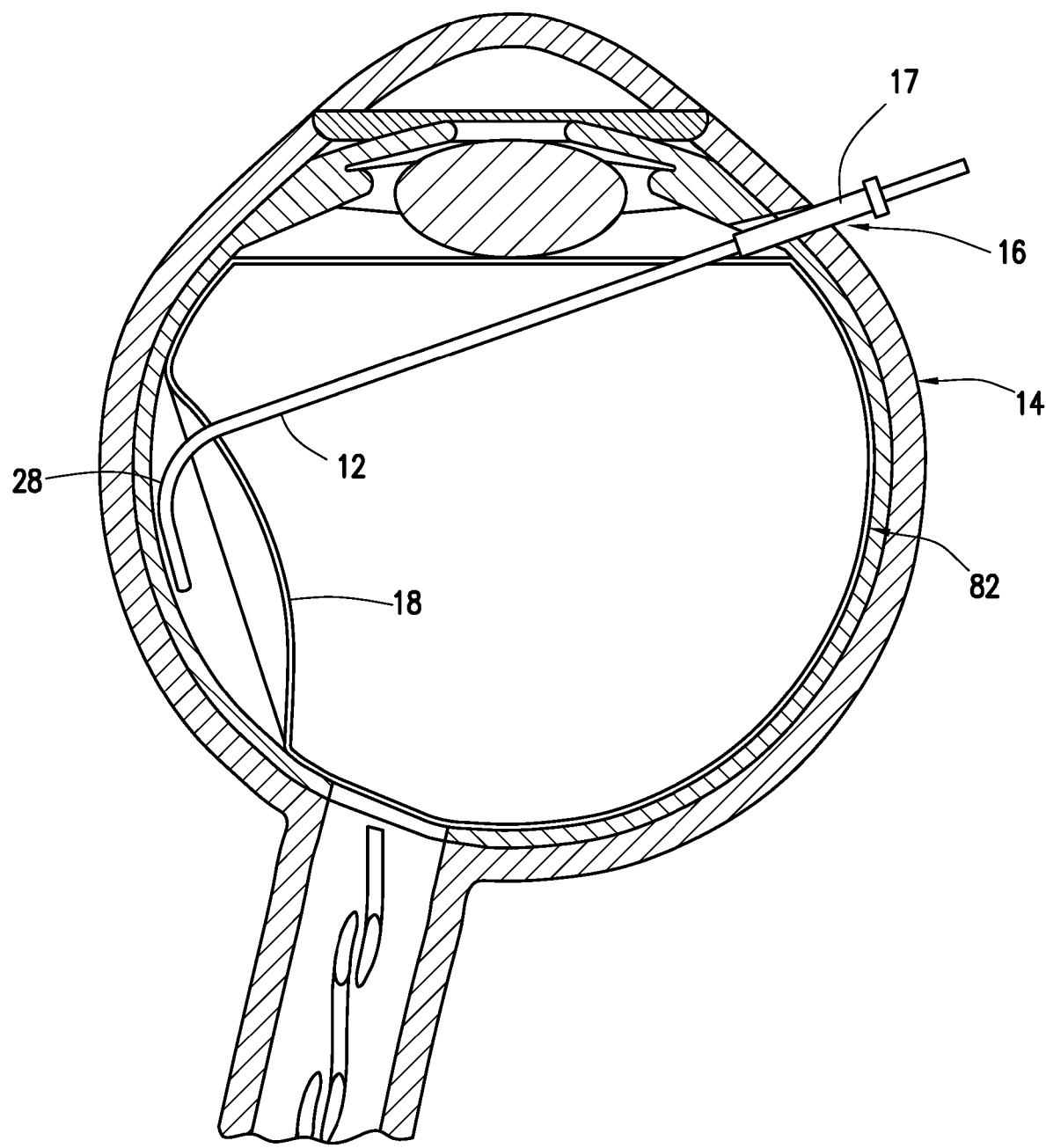
FIG. 2 illustrates a cross-sectional view of an eye in which a cannula of an example vitreoretinal instrument extends into the eye.

FIG. 1 illustrates an example vitreoretinal instrument 10. The vitreoretinal instrument 10 may include a cannula 12. As illustrated in FIG. 2, during an ophthalmic surgical procedure, the cannula 12 may be positioned within an eye 14 through an incision 16 by way of access cannula 17. In some instances, the access cannula 17 may be a component separate from the cannula 12. While present in the eye 14, the cannula 12 may be used to aspirate materials from the eye 14. For example, during a vitreoretinal surgery, the cannula 12 may be inserted into the eye 14 behind retina 18 to drain subretinal fluid.

Referring again to FIG. 1, the vitreoretinal instrument 10 may also include a handle 26 having a proximal end 20 and a distal end 22. Tubing 24 may extend from proximal end 20 of handle 26. The cannula 12 may extend from the distal end 22 of the handle 26. The cannula 12 may be directly or indirectly coupled to the handle 26. The cannula 12 may include a curved portion 28 at a distal end 29 and a straight portion 30 at a proximal end 31. The curved portion 28 may be configurable between a straight configuration and a curved configuration. With reference to FIG. 2, when the curved portion 28 is disposed in or otherwise passes through the access cannula 17, the curved portion 28 straightens into the straight configuration. As the cannula 12 is extended past the access cannula 17 into the eye 14, the curved portion 28 curves into the curved configuration. The amount by which the curved portion 28 curves varies with an amount by which the curved portion 28 extends from the access cannula 17. Thus, the curved configuration encompasses the curved portion 28 being in various degrees of curvature. As described in more detail below with respect to FIG. 7, the curved portion 28 of the cannula 12 curves so as to define an Angle A between a longitudinal axis 35 of the distal end 29 and a longitudinal axis 37 of the straight portion 30. In some implementations, with the cannula 12 fully extended from the access cannula 17, the angle A may be within a range of about 88° to about 92°. However, in other implementations, the angle A may be selected to be any desired angle. Further, in other implementations, the angle A may be adjusted depending on the length that the cannula 12 is extended from the access cannula 17. Thus, in some instances, when fully extended, the angle A of may be about 88° to 92° (although, as indicated above, the angle A may be any desired angle), while, when the cannula 12 is fully retracted into the cannula 17, the angle A may be within the range of about 0° to about 1° (although, this angle may similarly be selected to be any desired angle). The above-described behavior of the curved portion 28 of the cannula 12, i.e., the manner in which the curved portion 28 is alterable between the straight configuration and the curved configuration, is also applicable in the context of an outer tube, such as outer tube 13 shown in FIG. 4C and described in more detail below.

Figure 3A:
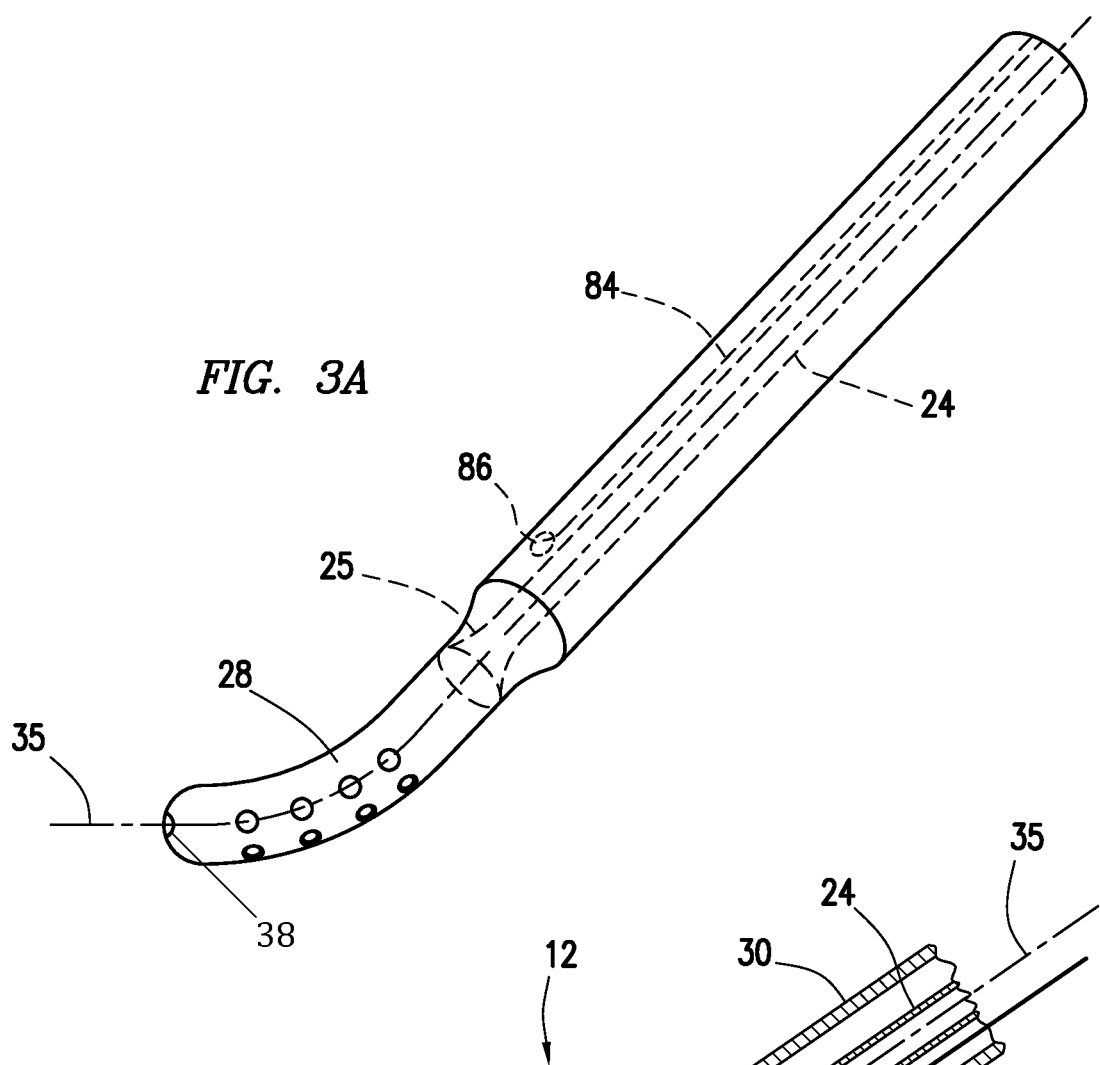
FIG. 3A is an enlarged, perspective, schematic view of the cannula of the vitreoretinal instrument of FIG. 1.

FIG. 3A shows a detail view of the cannula 12 of FIG. 1 in the curved configuration. As shown, the curved portion 28 may include a tip port 32 that is in fluid communication with a lumen 33 of the cannula 12. In some embodiments, the tip port 32 may have a surface 38 that is smooth and convex for interfacing with the retina 18 (e.g., shown on FIG. 2). The curved portion 28 may also include lateral ports 34a-34d on one side that open to the lumen 33 of the cannula 12. The lateral ports 34a-34d are located at the distal end 29 of the cannula 12. As a result of the curvature in the curved portion 28 of the cannula 12, the lateral ports 34a-34d are also angularly and laterally offset from the straight portion 30 of the cannula 12 when the curved portion 28 is in the curved configuration. In some implementations, the lateral ports 34a-34d may be slightly recessed from an exterior surface 36 of the curved portion 28.

Figure 3B:
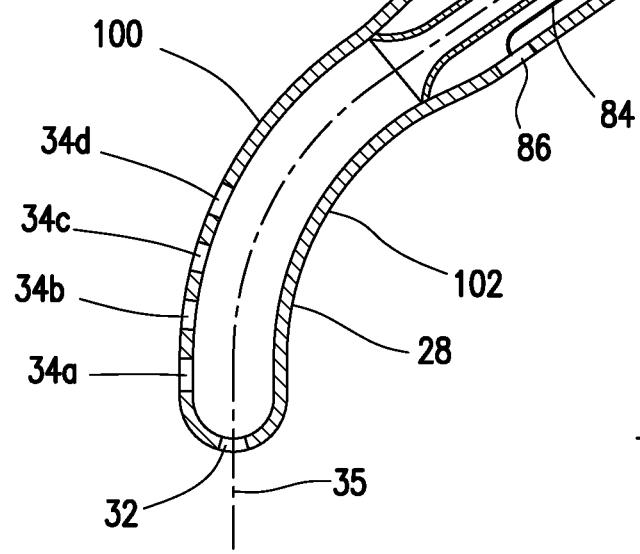
FIG. 3B shows a cross-sectional side view of a distal end of another example cannula.

FIG. 3B is a cross-sectional side view of another example cannula 12 that is similar to the cannula 12 shown in FIG. 3A. The cannula 12 includes a curved portion and straight portion 30 the, together, define a longitudinal axis 35. The longitudinal axis 35 defines a plane that divides the cannula 12 into two halves. The curved portion 28 defines an outer curvature 100 and an inner curvature 102. A single row of lateral ports 34a, 34b, 34c, and 34d are formed in the outer curvature 100 of the curved portion 28. By placing the lateral ports 34a, 34b, 34c, and 34d in this location, the risk of incarcerating the retina in the lateral apertures while the cannula 12 is removing subretinal fluid is reduced, because, when inserted through a tear in the retina, for example, the retina is located proximate to the inner curvature 102, which is on an opposite side of the curved portion 28 from the outer curvature 100. Further, in the illustrated example of FIG. 3B, the plane defined by the longitudinal axis 35 bisects the lateral ports 34a, 34b, 34c, and 34d. However, the scope of the disclosure is not so limited. Rather, referring again to FIG. 3A, the curved portion 28 includes two rows of lateral ports 34a-34d that are symmetrically arranged relative to and on opposite sides of the plane defined by the longitudinal axis 35. Thus, while the two rows lateral ports 34a-34d are symmetrically arranged relative to the plane defined by the longitudinal axis 35, the two rows of lateral ports 34a-34d are arranged circumferentially offset from the plane. In such implementations, the lateral ports 34a-34d are arranged along the outer curvature 100 but are angularly offset from along a circumference of the curved portion 28 away from the plane defined by the longitudinal axis 35. A row of lateral ports, such as a row of four lateral ports 34a, 34b, 34c, and 34d, may be angularly offset along the circumference of the curved portion 28 by up to 90° away from where the plane defined by the longitudinal axis 35 intersects the outer curvature 100. In some implementations the amount of angular offset may be less than 90°. For example, in some implementations, the amount of angular offset may be within the ranges of 0° to 10°; 10° to 20°; 20° to 30°; 30° to 40°; 40° to 50°; 50° to 60°; 60° to 70°; 70° to 80°; or 80° to 90°. With the arrangement of the lateral ports 34a-34d along the outer curvature 100 of the various examples described herein, the risk of incarceration of the retina into the lateral ports 34a-34d is reduced.

In some embodiments, the curved portion 28 may be elastic. By exhibiting elasticity, the cannula 12 may be configurable into and between the curved configuration and the straight configuration without permanent deformation. For example, the curved portion 28 may be extended and retracted through the access cannula 17 without permanent deformation. In some implementations, the curved portion 28 may be inserted into the eye 14 through access cannula 17 (e.g., shown on FIG. 2), where the curved portion 28 is converted from the initial, curved configuration into the straight configuration, and, once extended past the access cannula 17, the curved portion is again returned to the curved configuration without permanent deformation. The curved portion 28 may be made of an elastic material, such as, for example, a shape memory alloy, such as nickel titanium (also referred to as Nitinol). Other non-limiting examples of suitable elastic materials may include metals, plastics, super elastic materials, thermoplastic elastomers, or any combinations thereof. The straight portion 30 may be made from a material, including, for example, metals, plastics, or combinations thereof. In some embodiments, the straight portion 30 may be made of a metal such as stainless steel, for example. Without limitation, the straight portion 30 may be about 20 to about 27 gauge in size and may be made of a metal such as stainless steel.

Figure 3C:
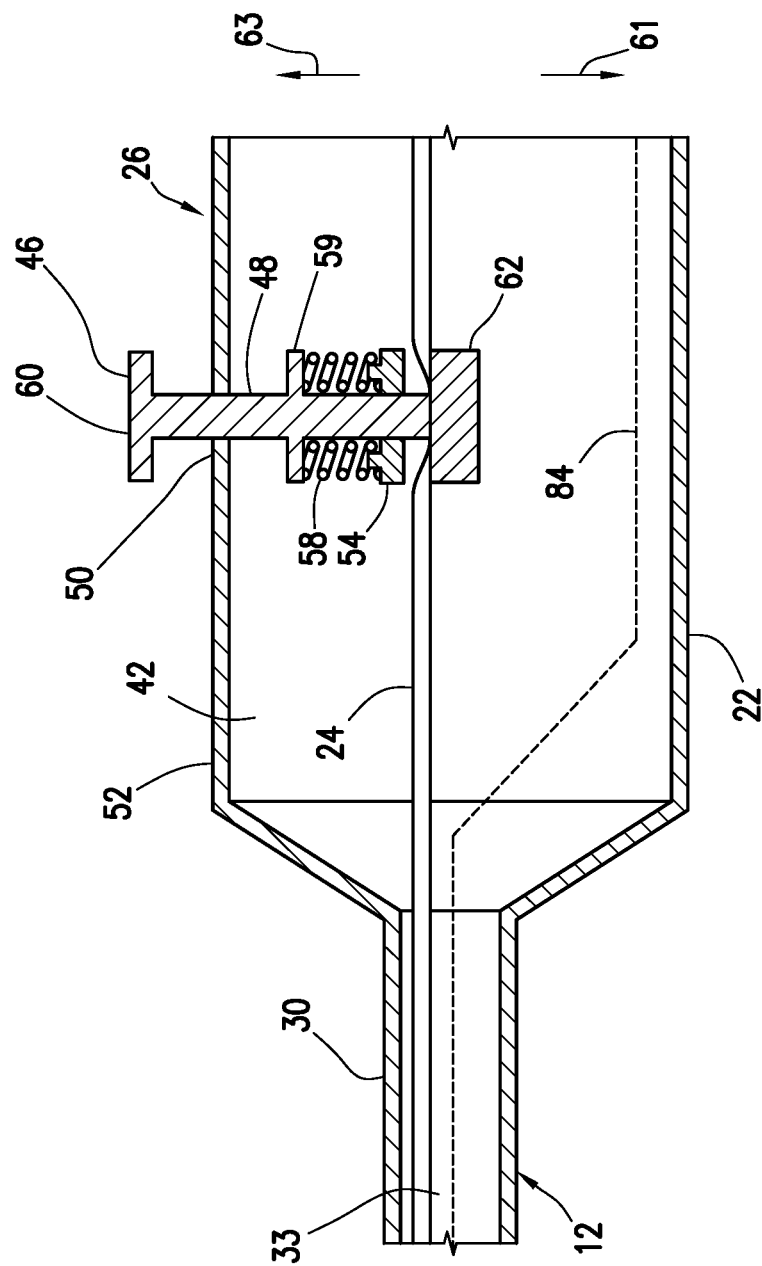
FIG. 3C is an enlarged, side, cross-sectional view of a portion of the vitreoretinal instrument of FIG. 1.

Referring to FIGS. 1 and 3C, the handle 26 also includes a compression valve 46, which may be actuated, for example, by a surgeon's finger. In some instances, the compression valve 46 may be actuated by a tip of the surgeon's middle finger, for example.

As shown in FIG. 3C, the compression valve 46 includes a piston 48 that is slidably disposed within an aperture 50 of a body 52 of the handle 26. A spring 58 may be disposed between a flange 59 of the piston 48 and a spring stop 54. The spring 58 may bias the piston 48 toward the aperture 50 by exerting a force against the piston 48. Accordingly, when the piston 48 is depressed in the direction of arrow 61, the force generated by the spring 58 increases, urging the piston 48 in the direction of arrow 63.

The handle 26 includes a lumen 42, which is fluidly coupled to the lumen 33 of the cannula 12. As illustrated, the tubing 24 is disposed within and extends through the lumen 42 and the lumen 33 of the cannula 12, as shown in FIG. 3A, for example. A portion of the tubing 24 is disposed against tubing support member 62. The spring stop 54 and the tubing support member 62 may be supported by the body 52. A distal end 25 of the tubing 24 may be fluidly coupled to lateral ports 34a-34d of the curved portion 28 (e.g., shown on FIG. 3A). As illustrated, the tubing 24 may terminate in the lumen 33 such that the distal end 25 may be fluidly coupled to the lateral ports 34a-34d by way of the lumen 33. Particularly, the distal end 25 forms a seal with an inner surface of the curved portion 28. In the illustrated example, the distal end 25 is flared and provides a seal with the inner surface of the curved portion 28. The compression valve 46 may be moveable between a first portion in which the tubing 24 is placed into an open configuration and a second position in which the tubing 24 is placed in a closed configuration.

Referring now to FIG. 1, a proximal end 27 of the tubing 24 is fluidly coupled to vacuum source 64. In some implementations, the tubing 24 may be a single tube. In other implementations, the tubing 24 may include multiple interconnected tubes. In some implementations, the vacuum source 64 may be disposed within an ophthalmic surgical console. In other implementations, the vacuum source 64 may be a separate or stand-alone device. The vacuum source 64 may provide a vacuum at a fixed value or a vacuum that is variable. For example, in some instances, the vacuum source 64 may provide a vacuum that varies proportionally with a position of a user input device (e.g., a footswitch) operatively coupled to the vacuum source 64 such as, for example, via connection of the vacuum source 64 and input device to an ophthalmic surgical console. In some implementations, one or more conventional syringes may be utilized as the vacuum source 64.

Referring to FIGS. 2, 3A, and 3C, the following describes an example method whereby a user, such as a surgeon or other medical professional, may use the vitreoretinal instrument 10 to aspirate subretinal fluid. For aspiration of subretinal fluid, the curved portion 28 may be placed into the subretinal space to aspirate the subretinal fluid. Subretinal fluid removal may be necessary in retinal detachment cases. In some implementations, a vitrectomy may be performed to gain access, for example, to the retinal detachment or tear. The user may position the cannula 12 of the vitreoretinal instrument 10 through the access cannula 17 and into the eye 14. Access for the cannula 12 into the subretinal space may be gained through the pre-existing retinal break or tear or via a retinectomy or retinotomy. If the tip port 32 is formed with a sharpened tip, in particular implementations, it may be used to perform such retinectomy or retinotomy. The curved portion 28 of the cannula 12 may be extended from the access cannula 17 once inside the eye 14 such that the curved portion 28 curves into the curved configuration. The curved portion 28 may be disposed close to the retina 18 (e.g., shown on FIG. 2), and the lateral ports 34a-34d may be disposed under the retina 18 in the subretinal space. The user may press down on the actuating surface 60 of the compression valve 46 so that the piston 48 closes the tubing 24 against the tubing support member 62 and precludes aspiration. The user then may activate the vacuum source 64 and may aspirate subretinal fluid via the tip port 32, the lateral ports 34a-34d, and the tubing 24 by use of the compression valve 46 to control the vacuum. The spring 58 may bias the piston 48 in the direction of arrow 63 to open the tubing 24 as pressure on the actuating surface 60 is released. The spring 58 may bias the piston 48 to open the tubing 24 and provide the vacuum to the tip port 32 and the lateral ports 34a-34d, aspirating subretinal fluid. Aspiration of the subretinal fluid may continue via the tip port 32, the lateral ports 34a-34d, and the tubing 24.

With continued reference to FIGS. 3A and 3C, the user may also use the tip port 32 and the lateral ports 34a-34d, to express subretinal fluid, mobilize and/or smooth out retinal folds, unfold retinal tears and/or retinectomy flaps, or help to cause the retina 18 to flatten against the choroid 82 in the proper location. The surface 38 of the tip port 32 and a surface 39 of the lateral ports 34a-34d may be smooth and have low friction to avoid damage to the retina 18. In addition, the surface 38 of the tip port 32 and the surface 39 of the lateral ports 34a-34d may be coated with, made from, or include polytetrafluoroethylene, silicone, or other friction reducing material to avoid adherence to the retina 18, retinal pigment epithelium, or the choroid 82 thereto.

In addition, an optical fiber 84 may be disposed in the handle 26 and extend into the cannula 12. In the illustrated example, the optical fiber is disposed within the lumen 33 of the cannula 12 but exterior to the tubing 24. In some implementations, the straight portion 30 of the cannula 12 may be formed with a light transmitting window 86, or all or part of the curved portion 28 may be formed from a light transmitting material, such as, for example, a plastic, so that the vitreoretinal instrument 10 may provide intraocular illumination for the user when the optical fiber 84 is operatively coupled to a light source (not shown). Such illumination may allow the user to avoid the need to use a separate endoilluminator to provide illumination. Consequently, the user is able to hold another microsurgical instrument with his or her other hand, if desired. In some implementations, the light transmitting window 86 or light transmitting material may be transparent. In the illustrated example, the light transmitting window 86 is disposed within the straight portion 30 and on a side of the straight portion 30 that corresponds with the inner curvature 102, as shown, for example, in FIGS. 3A and 3B. In some instances, the distal end of the optical fiber 84 is disposed adjacent to the light transmitting window 86.

Figure 4A:
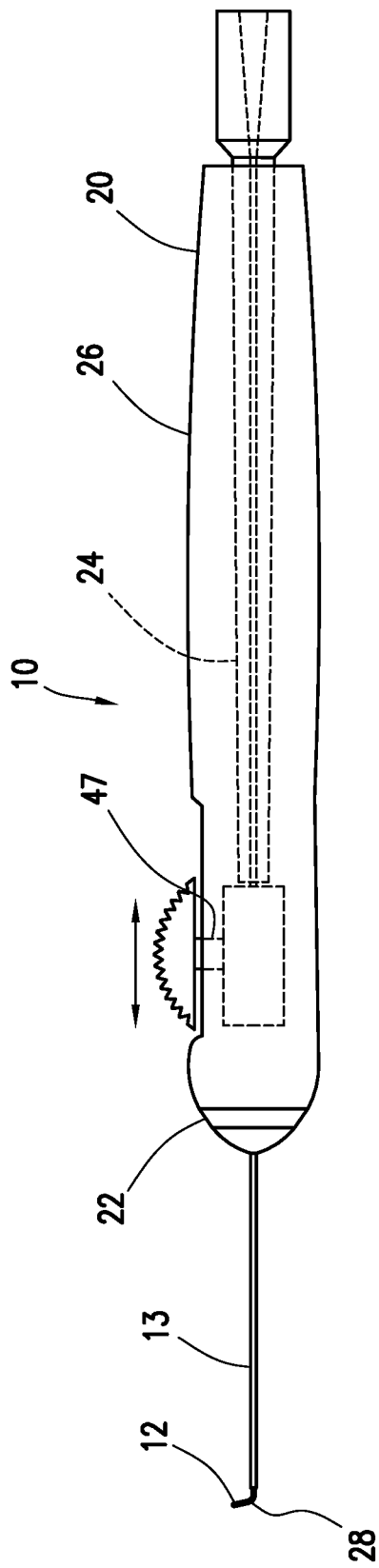
FIG. 4A illustrates another example vitreoretinal instrument.
Figure 4B:
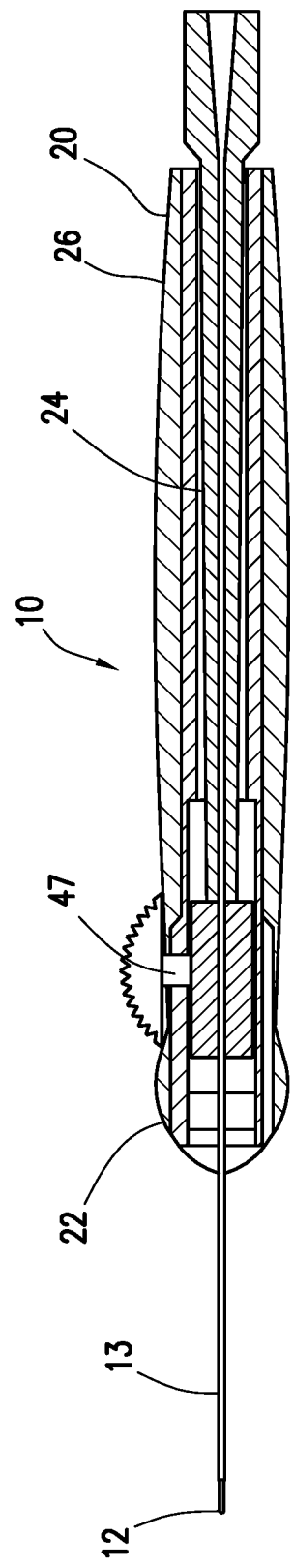
FIG. 4B illustrates a curved portion of the vitreoretinal instrument of FIG. 4A at least partially retracted into an outer tube.
Figure 4C:
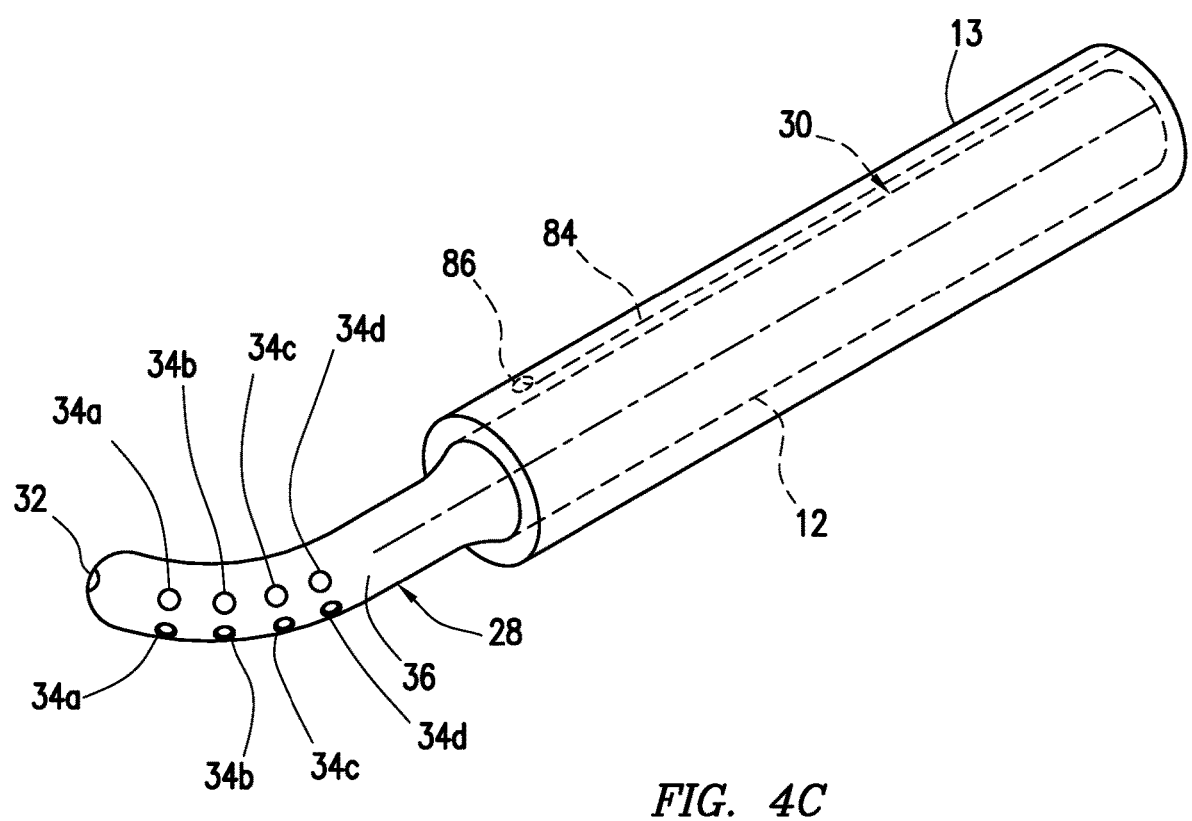
FIG. 4C illustrates a cannula and an outer tube of the vitreoretinal instrument of FIG. 4A.

FIGS. 4A-4C show another example of the vitreoretinal instrument 10. In the illustrated embodiment, the vitreoretinal instrument 10 further includes an outer tube 13 extending distally from the handle 26. The cannula 12 is disposed in and is moveable though the outer tube 13. Particularly, the cannula 12 is extendable from and retractable into the outer tube 13. As shown in FIGS. 4A and 4C, the cannula 12 curves into the curved configuration when it is extended from the outer tube 13. As the cannula 12 is retracted into the outer tube 13, the curved portion 28 of cannula 12 straightens into the straight configuration. As shown in FIG. 4B, the curved portion 28 is shown straightened as the cannula 12 is retracted into the outer tube 13. Although FIG. 4B shows the curved portion 28 as being fully straight with a portion of the curved portion 28 still extending from the outer tube 13, the scope of the disclosure is not so limited. Rather, in some instances, a curvature of the curved portion 28 may continually or progressively straighten as the cannula 12 is retracted. When fully retracted, the curved portion 28 may be straight or generally straight. As the cannula 12 is extended from the outer tube 13, the curved portion 28 curves into the curved configuration as shown, for example, in FIG. 4A. That is, as the cannula 12 is extended from the outer tube 13, the cannula 12 continues progressively to form a curved shape until fully extended, at which point the cannula 12 is completely has fully attained the curved configuration. FIG. 4C shows the cannula 12 fully extended from the outer tube 13 and configured in the curved configuration. The cannula 12 may be flexible and may bend back to its curved configuration once extended from the outer tube 13. While not shown, the cannula 12 may be retracted into the outer tube 13 for insertion through an incision and extended from the outer tube 13 once in the eye 14.

Referring to FIGS. 4A and 4B, in this example, the handle 26 includes a mechanism 47. The mechanism 47 is operable to extend the cannula 12 from the outer tube 13 as the mechanism 47 is slid towards the distal end 22 of the handle 26. As the cannula 12 is extended from the outer tube 13, the curved portion 28 of the cannula 12 may curve into the curved configuration. Sliding the mechanism 47 towards the proximal end 20 of the handle 26 retracts the cannula 12 into the outer tube 13. In some embodiments, the curved portion 28 may be elastic in nature such that the curved portion 28 may be in the straight configuration when retracted into the outer tube 13 and then revert to the curved configuration when extended from the outer tube 13.

FIG. 8 shows another example vitreoretinal instrument 200 in which the optical fiber 84 is embedded within the outer tube 13. In this example, the outer tube 13 includes a groove or recess 210 formed in a distal end 220 of the outer tube 13. The optical fiber 84 terminates at a wall 230 of the groove 210. However, in other instances, the distal end 220 of the outer tube 13 may include a notch 240 that defines the wall 230. The distal end 250 of the optical fiber 84 is exposed at the wall 230, and light is emitted from the distal end 250 of the optical fiber 84 to provide illumination such as during a surgical procedure.

FIG. 9 is an example vitreoretinal instrument 300 in which the optical fiber 84 is embedded in the outer tube 13. The distal end 250 of the optical fiber 84 terminates at the exterior surface 310 of the outer tube 13. In some instances, the distal 250 may be exposed at the outer surface 310 of the outer tube 13. In other instances, a light transmitting window 86 may be formed or otherwise disposed in the outer tube 13. The light transmitting window 86 permits transmission of light emitted from the distal end 250 of the optical fiber 86 and provides illumination, such as during a surgical procedure.

Figure 5A:
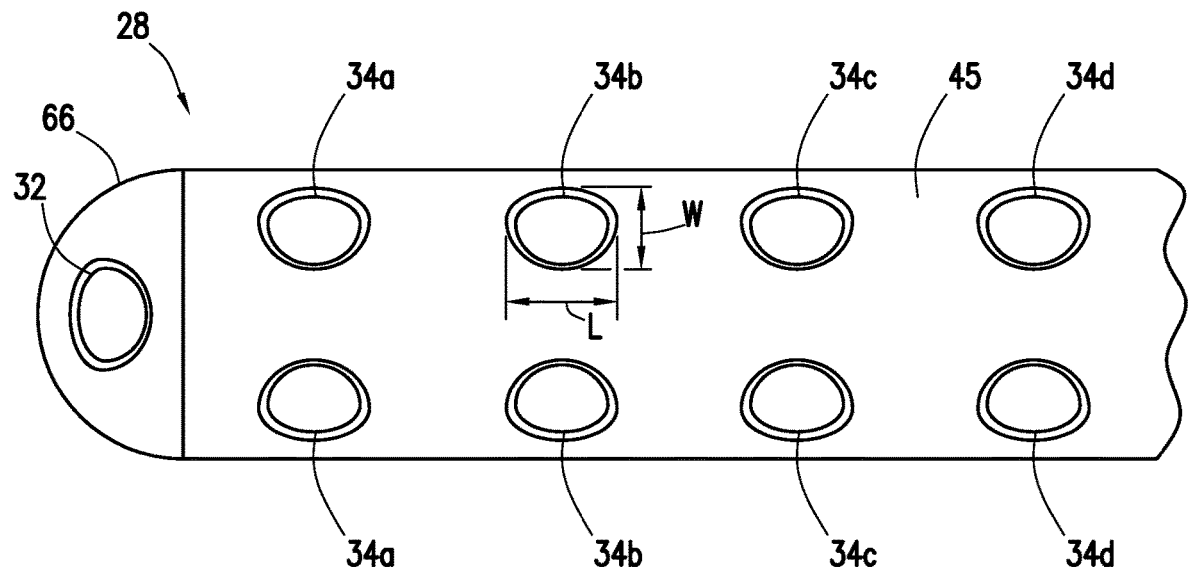
FIG. 5A illustrates a curved portion of an example vitreoretinal instrument.

FIG. 5A illustrates a detail view of an example embodiment of the curved portion 28. The curved portion 28 includes the tip port 32 formed in a distal tip 66 of the curved portion 28 and the lateral ports 34*a*-34*d* formed in the curved portion 28. In some implementations, the diameter of the tip port 32 may range from about 0.10 mm to about the diameter of the tubing 24, for example, up to about 0.4 mm (e.g., shown on FIG. 1). In other implementations, the curved portion 28 may include the tip port 32 but exclude the lateral ports 34*a*-34*d*. As illustrated, the curved portion 28 includes eight of the lateral ports 34*a*-34*d*. In alternate embodiments, the curved portion 28 may include more or less than eight of the lateral ports 34*a*-34*d*. As illustrated, the lateral ports 34*a*-34*d* may be evenly spaced. In alternative embodiments (not shown), the spacing of the lateral ports 34*a*-34*d* may vary. By way of example, the spacing of the lateral ports 34*a*-34*d* may increase or decrease moving toward the distal tip 66. The tip port 32 and the lateral ports 34*a*-34*d* may be of the same size. In other implementations, the size of the lateral ports 34*a*-34*d* may vary from each other. Further, the size of one or more or all of the lateral ports 34*a*-34*d* may be different from the size of the tip port 32. Without limitation, the lateral ports 34*a*-34*d* may have a spacing of from about 0.05 mm to about 0.4 mm. Without limitation, the tip port 32 and the lateral ports 34*a*-34*d* may individually have a diameter of from about 0.10 mm to about 0.4 mm. As illustrated, the lateral ports 34*a*-34*d* may be arranged in a pair of rows on the curved portion 28. However, it should be understood that lateral ports 34*a*-34*d* may be arranged in more or less than two rows. In some implementations, the rows of lateral ports 34*a*-34*d* may be diametrically opposed to each other. In other implementations, the rows of lateral ports 34*a*-34*d* may be angularly offset from each other by more or less than 180° about a centerline of the curved portion 28.

Figure 5B:
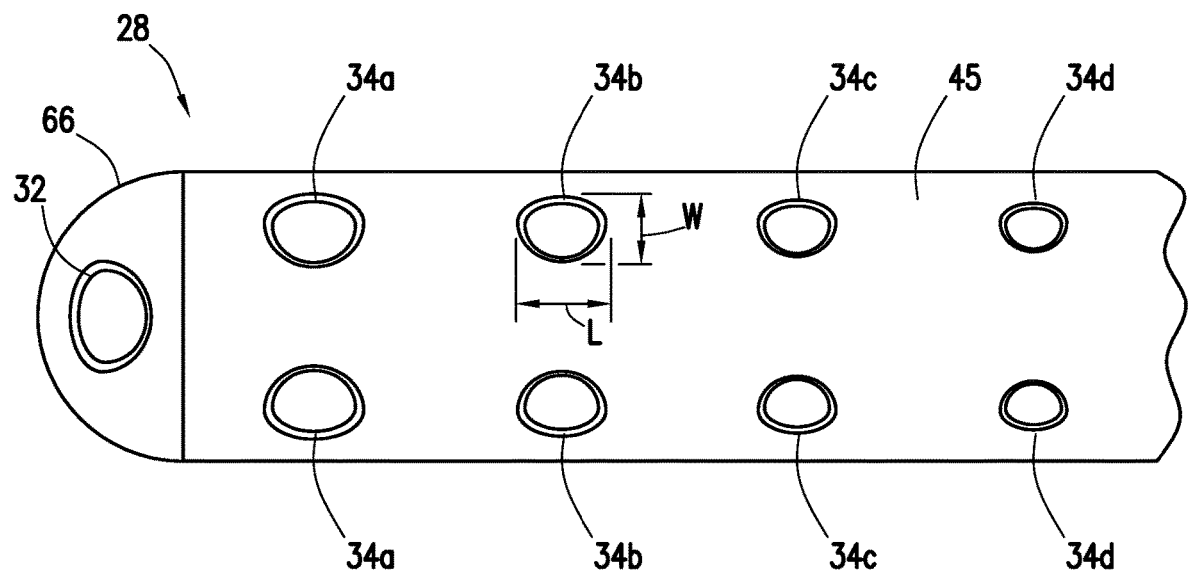
FIG. 5B illustrates another example of a curved portion of a vitreoretinal instrument with ports having varying sizes.

FIG. 5B illustrates a detail view of another embodiment of the curved portion 28 with the lateral ports 34*a*-34*d* having varying sizes. In some implementations, the lateral ports 34*a*-34*d* may have circular shapes, and, hence, the varying sizes of the lateral ports 34*a*-34*d* may be varying diametrical sizes. However, in other implementations, the shapes of the lateral ports 34*a*-34*d* may be other than circular. For example, in some implementations, the lateral ports 34*a*-34*d* may be elliptical, rectangular, square, or any other shape.

Referring again to FIG. 5B, the curved portion 28 includes the tip port 32 formed in the distal tip 66 and the lateral ports 34*a*-34*d* formed in the curved portion 28. As illustrated, the ports (e.g., tip port 32 and lateral ports 34*a*-34*d*) in the curved portion 28 may decrease in size from the distal tip 66 towards a proximal end of the curved portion 28. The tip port 32 may be the largest and with increasing distances from the distal tip 66, the size of the lateral ports 34*a*-34*d* may decrease. The changes in size of the ports may distribute the flow equally over all the lateral ports 34*a*-34*d* without any maxima in vacuum and reduced suction force. In some embodiments, the tip port 32 may have the largest size, e.g., diameter; the size, e.g., diameter, of the lateral ports 34*a* may be smaller than the size of the tip port 32; the size, e.g., diameter, of the lateral ports 34*b* may be smaller than the size of the lateral ports 34*a*; the size, e.g., diameter, of the lateral ports 34*c* may be smaller than the size of the lateral ports 34*b*; and the size, e.g., diameter, of the lateral ports 34*d* may be smaller than the size of the lateral ports 34*c*. In some implementations, the lateral ports 34*d*, which are shown as being the furthest away from the tip port 32, may have the smallest size. In some instances, the spacing and size of the lateral ports 34*a*-34*d* in this configuration may be the same as described above with respect to FIG. 5A. By decreasing a size of the ports by about 5% to about 10%, for example, from the distal tip 66 towards a proximal end of the curved portion 28, a pressure at the different ports, e.g., tip port 32 and lateral ports 34*a*-34*d*, may be balanced so that fluid pressure at each port is the same or about the same. In still other instances, sizes of the lateral ports 34*a*-34*d* may increase with increasing distance proximally from the distal tip 66. Thus, in some instances, the size of the lateral ports 34*a* may be smaller than the size of the lateral ports 34*b*, which may be smaller than a size of the lateral ports 34*c*, which may be smaller than a size of the lateral ports 34*d*.

Figure 5C:
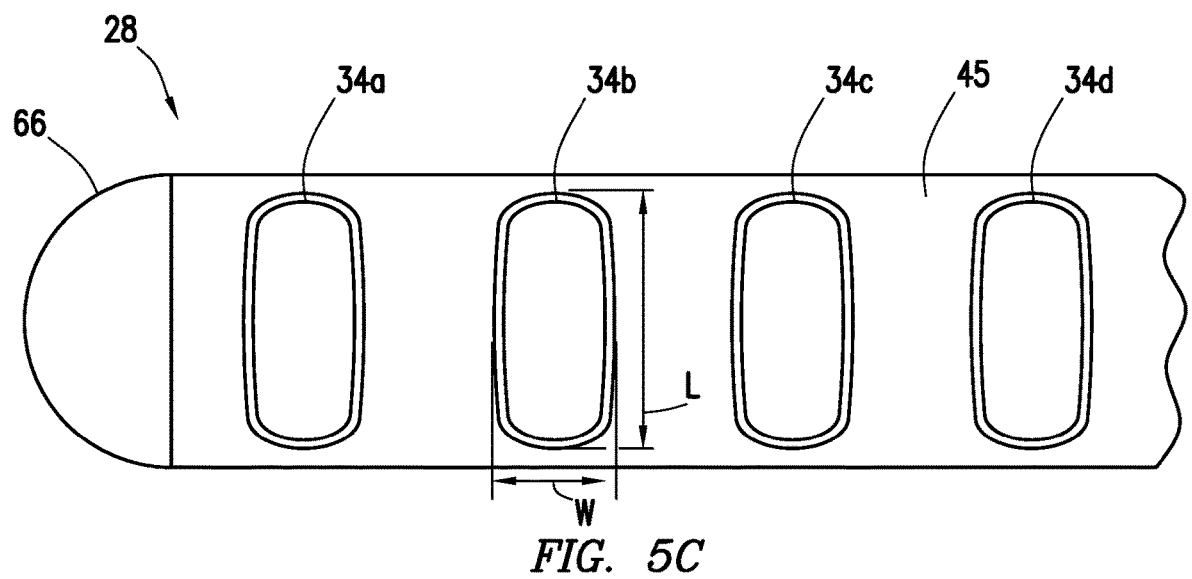
FIG. 5C illustrates an example curved portion of a vitreoretinal instrument with ports in a four wave configuration.

FIG. 5C illustrates a detail view of an alternate embodiment of the curved portion 28 with the lateral ports 34*a*-34*d* being oval or elliptical in shape. The lateral ports 34*a*-34*d* may be referred to as being in a wave configuration as a result of the lateral ports 34*a*-34*s* being elliptical in shape ("waves"). As illustrated, the curved portion 28 does not include a port formed in the distal tip 66. The lateral 28 ports 34*a*-34*d* may have any desired spacing, for example, including from about 0.1 mm to about 0.5 mm. In some embodiments, spacing between at least two of the adjacent lateral ports 34*a*-34*d* may be about 0.3 mm. However, the scope of the disclosure is not so limited. Rather, the spacing between adjacent lateral ports may be any desired spacing. Further, in some implementations, the spacing may be uniform between adjacent lateral ports. In other implementations, the spacing between adjacent lateral ports may vary.

The lateral ports 34a-34d may be any desired size. For example, in some implementations, the lengths L and/or widths W of one or more of the lateral ports 34a-34d at outer surface 45 of the curved portion 28 may range from about 0.05 mm to about 0.5 mm. For embodiments with the lateral ports 34a-34 being oval or elliptical in shape, the length L may be defined as the major axis and the width W may be defined as the minor axis. In some embodiments, one or more of the lateral ports 34a-34d may be about 0.1 mm in width W and about 0.3 mm in length L. Again, though, the width and length of the lateral ports may be any desired size. Further, in some implementations, the size of the lateral ports may be uniform. In other implementations, sizes of the lateral ports may vary. For example, in some implementations, a size of the lateral ports may decrease along a length of the curved portion 28 in the distal direction. Without limitation, one or more of the lateral ports 34a-34d that are elliptical in shape may define an opening having an area of from about 0.01 mm$^2$ to about 0.05 mm$^2$. However, the scope of the disclosure is not so limited. Rather, the opening area of one or more of the lateral ports 34a-34d at the outer surface 45 may be any desired size. Further, although FIG. 5C shows four lateral ports, in other implementations, there may be more or fewer than four lateral ports 34a-34d.

Figure 7:
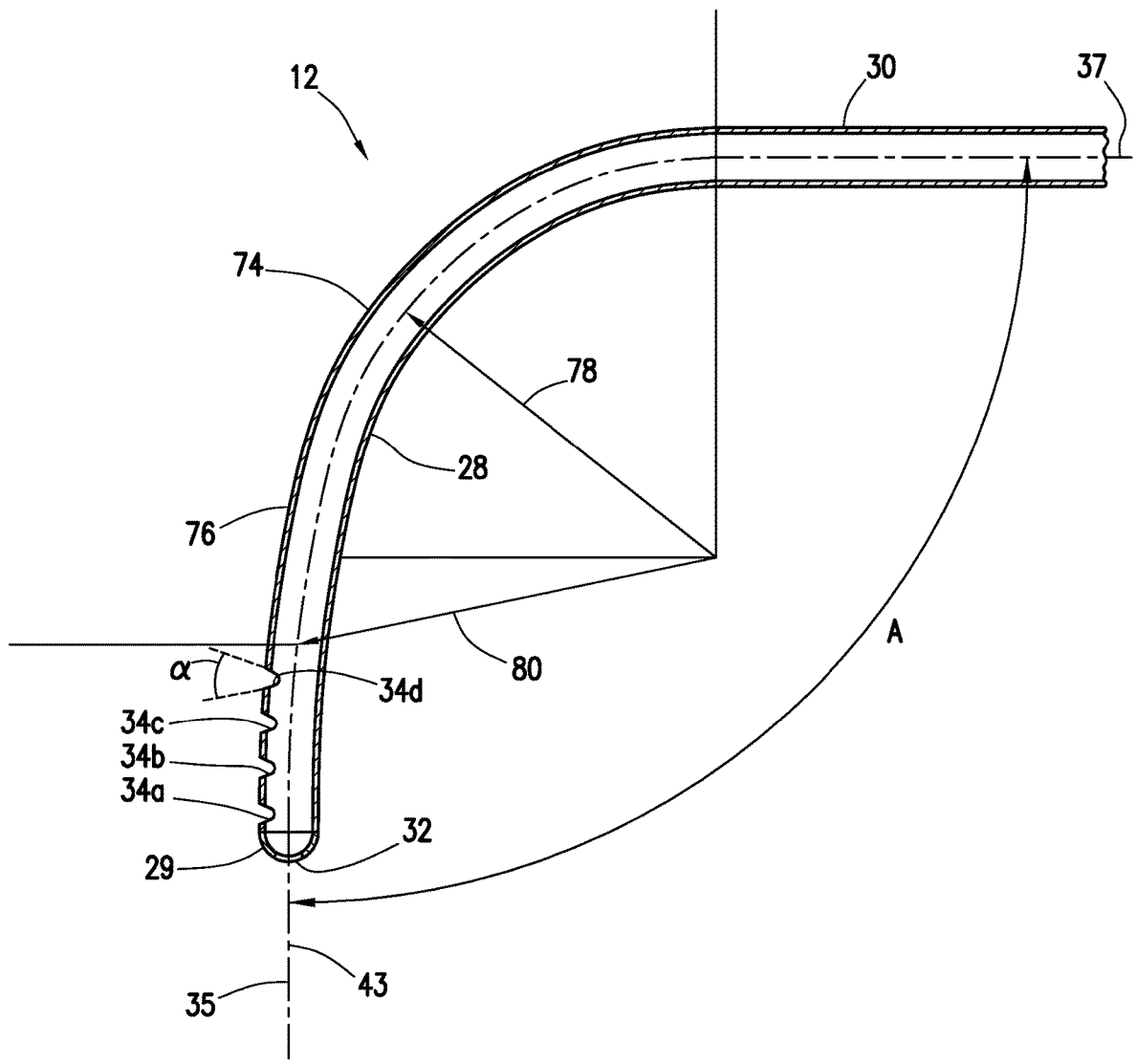
FIG. 7 illustrates an example of a cannula of a vitreoretinal instrument.

As illustrated, the lateral ports 34a-34d, in some implementations, are elliptical or oval in shape and are arranged on the curved portion 28 in a single row. However, in other implementations, the lateral ports may be arranged differently. For example, in some instances, the lateral ports 34a-34d having a wave configuration (i.e., oval or elliptical in shape) may be arranged in more than one row. In some embodiments, an opening angle (e.g., opening angle α shown in FIG. 7) of oval or elliptical lateral ports 34a-34d may be generally smaller than the opening angle for the lateral ports 34a-34d having circular shapes such as those, for example, shown in FIGS. 5A and 5B. The opening angle is defined as the angle made by the sides of a lateral port when viewed along a cross section taken through the lateral port, as shown in FIG. 7. Without limitation, an opening angle of one or more of the lateral ports 34a-34d may range from about 0° to about 40°. However, the scope of the disclosure is not so limited, and the size of the opening range may be larger than 40°. Larger opening angles may improve a flow rate through a lateral port. In some embodiments, the lateral ports 34a-34d may include an opening angle of about 40°. The elliptical or oval shape may allow for a larger total open area compared to that of the lateral ports shown in FIGS. 5A and 5B, for example. Further, a curved portion 28 having oval or elliptical lateral ports may provide a greater number of ports over a given length (e.g., along a longitudinal axis of the curved portion 28) compared to lateral ports having a circular shape. During use, when the outer radius of the curved portion 28 is oriented against the choroid 82 (e.g., shown on FIG. 2), the vacuum pressure communicated by each the lateral ports may be reduced as the number of lateral ports is increased.

Figure 5D:
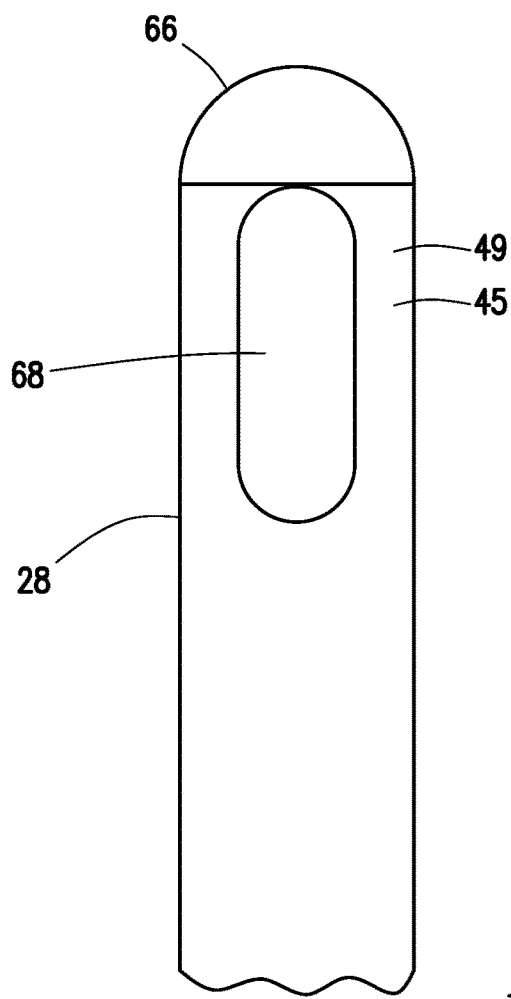
FIG. 5D illustrates an example of a curved portion of a vitreoretinal instrument with a single elongated port.

FIG. 5D illustrates a detail view of yet another alternate embodiment of a curved portion 28. In the illustrated embodiment, the curved portion 28 includes a single elongated port 68 formed in the curved portion 28, instead of the lateral ports 34a-34d. The single elongated port 68 may be formed along longitudinal axis 35 and along a circumferential portion 49 of the outer surface 45 of the curved portion 28. As illustrated, the distal tip 66 of the curved portion 28 is unperforated and, as such, does not include the tip port.

Figure 6A:
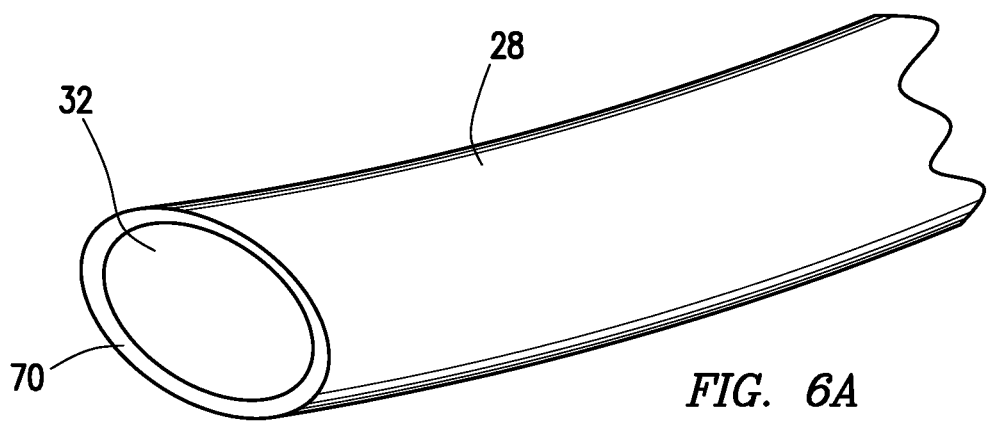
FIG. 6A illustrates an example of a curved portion of a vitreoretinal instrument with a tip port that is beveled.
Figure 6B:
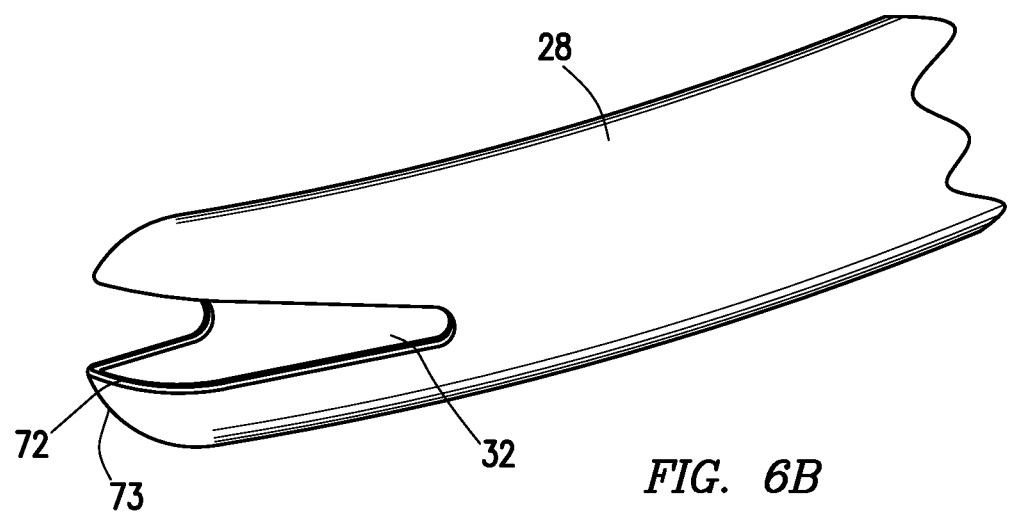
FIG. 6B illustrates an example of a curved portion of a vitreoretinal instrument with a tip port that is double beveled.
Figure 6C:
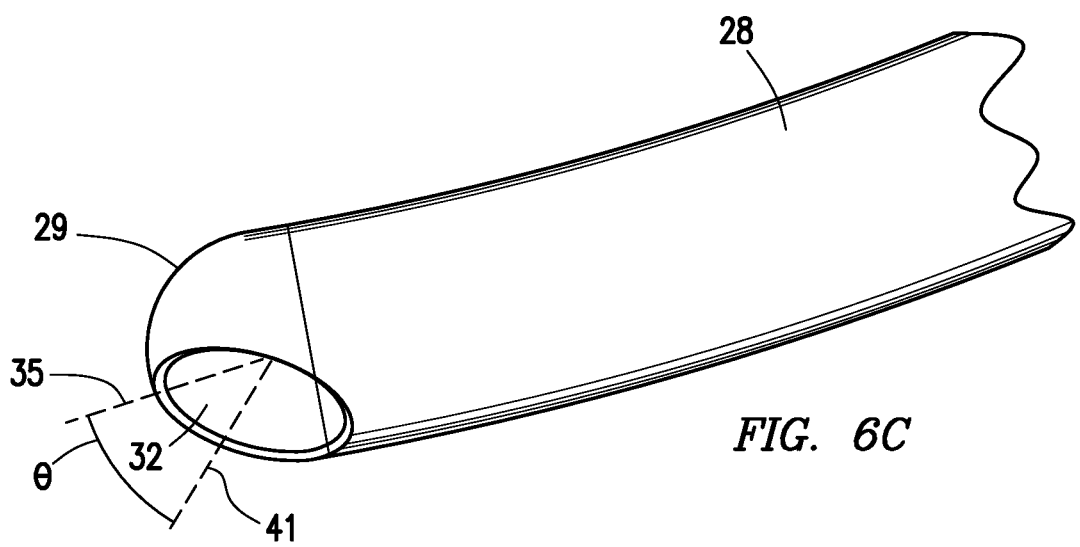
FIG. 6C illustrates an example of a curved portion of a vitreoretinal instrument with a tip port that is positioned on a bottom portion of the curved portion.

In addition to varying the configuration of the lateral ports 34a-34d, the configuration of the tip port 32 may also be varied. FIGS. 6A to 6C illustrate detail views of embodiments of the curved portion 28 with different configurations for the tip port 32. FIG. 6A illustrates an embodiment of the curved portion 28 in which the tip port 32 has a beveled surface 70. Configurations of the ports (e.g., tip port 32, lateral ports 34a-34d) shown in FIGS. 3A, 4C, 5A, 5B, 5C, 5D, and 7, for example, of the present disclosure reduces vacuum pressure at each of the ports formed in the curved portion 28 at retina 18 (e.g., shown on FIG. 2) in order to avoid incarceration of the retina 18 by or into any of the ports. However, the configuration of the tip port 32 in FIG. 6A may allow for maximal flow but less reduction in vacuum pressure to which the retina may be exposed. The tip port 32 may include a large opening for maximum flow and a beveled surface 70 for protection of the retina 18.

FIG. 6B illustrates a detail view of an alternate embodiment of curved portion 28 in which tip port 32 has a double beveled surface 72 that form a slit at a distal tip 73 of the curved portion 28. The configuration of the tip port 32 in FIG. 6B may be optimized to reduce a vacuum pressure to which the retinal and RPE/choroid may be exposed. The configuration of the tip port 32 may include the double beveled surface 72 to protect the retina 18 and the choroid 82 (e.g., shown on FIG. 2).

FIG. 6C illustrates a detail view of an alternate embodiment of the curved portion 28 in which the tip port 32 is oriented at an angle θ that is offset from longitudinal axis 35 of the distal end 29. As illustrated in FIG. 6C, the tip port 32 has a central axis 41 that is angularly offset from the longitudinal axis 35 of the cannula 28. In some implementations, the angle θ formed between the central axis 41 of the tip port 32 and the longitudinal axis 35 may be up to about 70°. In the illustrated example, the angle θ is located in the plane defined by the longitudinal axis 35. In some implementations the angle θ may be within the range of 0° to 10°, 0° to 20°, 0° to 30°, 0° to 40°, 0° to 50°, 0° to 60°, 0° to 70°, 0° to 80°, 0° to 90°, or any angle within any of these ranges. The angular offset between the tip port 32 and the longitudinal axis 35 may protect the retina by reducing the risk of incarcerating the retina by the tip port 32.

Although the example cannulas 12 shown in FIGS. 6A-6B as having a tip port 32 and excluding any lateral ports, other implementations may include a tip port 32 of a type shown in FIGS. 6A-6B while also including one or more lateral ports, such as one or more lateral ports 34a-34d shown, for example, in FIG. 3A, 4C, 5A, 5B, 5C, 5D, or 7. The included lateral ports may be configured in a manner as described herein.

FIG. 7 illustrates the cannula 12 of the vitreoretinal instrument 10 (e.g., shown in FIG. 1 or FIG. 4C) in the curved configuration in more detail. As illustrated, the cannula 12 comprises a curved portion 28 and a straight portion 30. The curved portion 28 includes one or more ports, including the tip port 32 in the distal end 29 of the curved portion 28 and the lateral ports 34a-34d formed in the curved portion 28. The lateral ports 34a-34d have an opening angle α as shown on FIG. 7. In the illustrated embodiment, the curved portion 28 includes a first curved portion 74 and a second curved portion 76. The second curved portion 76 may be closer to the distal end 29 of the cannula 12 than the first curved portion 74. The first curved portion 74 and the second curved portion 76 may have different radii of curvatures. For example, the first curved portion 74 may have a curvature defined by a first radius 78, and the second curved portion 76 may have a curvature defined by a second radius 80. The second radius 80 may be larger than the first radius 78. The first radius 78 may range, for example, from about 2 mm to about 4 mm. In some embodiments, the first radius 78 may be about 2.56 mm. The first curved portion 74 may be formed to adjust the angle of the distal end 29 along the choroid 82 (e.g., shown on FIG. 2). The second curved portion 76 may be formed so as to conform to the shape of the choroid 82. The second radius 80 may range, for example, from about 8 mm to about 10 mm. In some instances, the first radius 78 and the second radius 80 may be the same size.

As further illustrated on FIG. 7, the curved portion 28 of the cannula 12 curves so as to define the angle A between a portion 43 the longitudinal axis 35 at the distal end 29 and a portion 37 of the longitudinal axis 35 at the straight portion 30. In some implementations, the curved portion 28 may curve such that the angle A may be within a range of about 88° to about 92°, such as when the curved portion 28 is fully extended from the access cannula 17 or the outer tube 13. However, this angle A may also be adjusted as desired for a particular application. For example, the curved portion 28 may be formed or otherwise shaped such that the angle A may be less than about 88° or greater than about 92°. In addition, as previously described, curved portion 28 may be retracted into a channel, such as a channel defined by access cannula 17 (e.g., shown on FIG. 2) or outer tube 13 (e.g., e.g., shown on FIGS. 4A-4C). Curved portion 28 may be elastic so that the curved portion 28 may straighten when retracted into the channel but also return to a selected curvature after extension from the channel. Furthermore, the Angle A, together with the first radius 78 and the second radius 80, may be adjusted by varying the distance of extension of the curved portion 28 from the channel or retraction into the channel defined by the access cannula 17 or the outer tube 13. For example, depending on the distance of extension, the angle A may be adjusted from about 88° to 92°, which may be associated with the curved portion 28 being fully extended, to an angle of about 0° to about 1°, which may be associated with the curved portion 28 being fully or almost fully retracted into the channel (e.g., a channel defined by an access cannula or by an outer tube, such as outer tube 13). By varying the angle A, the vitreoretinal instrument 10 may allow for improved subretinal fluid aspiration by improved access of subretinal space/retinal break with less retinal incarceration. For example, the curve of curved portion 28 may be optimized to a desired angle A and with the lateral ports 34a-34d in parallel to the choroid 82 from the given insertion into the posterior segment of the eye 14.

As discussed above, it may be appreciated that the present disclosure may provide improved apparatus and methods for removing subretinal fluid. The vitreoretinal instrument 10 may maximize patient safety as well as the success of the surgical procedure by facilitating complete removal of subretinal fluid; preventing or reducing the likelihood of damage to the retina, retinal pigment epithelium, or choroid and facilitating the proper repositioning of retinal tears or detachments.

The present disclosure is illustrated herein by example, and various modifications may be made by a person of ordinary skill in the art. For example, although the compression valve 46 is described hereinabove with the piston 48 compressing the tubing 24 and precluding aspiration by tip port 32 and lateral ports 34a-34d when a user presses down on actuating surface 60 with his or her finger, other configurations may be used for control of aspiration. As another example, a different valve other than the compression valve 46 may be used for compression valve 46. As a further example, the present disclosure may also be used to perform air/gas exchanges typically performed in vitreoretinal surgery. As a further example, the lateral ports 34a-34d and the tip port 32 may be utilized to inject a surgical fluid or drug formulation, if desired. As a further example, the present disclosure is also applicable to other types of surgeries other than vitreoretinal surgery.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. A vitreoretinal instrument for use in removing subretinal fluid, comprising:
   a handle; and
   a cannula coupled to the handle, the cannula comprising:
      a straight portion;
      a curvable portion configurable between a straight configuration and a curved configuration, the curvable portion comprising an outer curvature and an inner curvature when the curvable portion is configured in the curved configuration, the curved configuration comprising:
         a first curved portion having a curvature defined by a first radius, wherein the curvature of the first curved portion angles a distal end of the curvable portion along a choroid; and
         a second curved portion having a curvature defined by a second radius, wherein the second radius is different from the first radius and wherein the curvature of the second curved portion conforms to a shape of the choroid;
   one or more ports formed in the curvable portion;
   an outer tube, wherein an entire outer tube is straight, and wherein the cannula is extendable and retractable within the outer tube, and wherein a shape of the curvable portion is variable between the curved configuration as the cannula is extended from the outer tube and the straight configuration as the cannula is retracted into the outer tube; and
   a mechanism on the handle to extend and retract the cannula from the outer tube;
   wherein the one or more ports comprise a plurality of lateral ports formed only along a length of a portion of the curvable portion and only along the outer curvature of the curved configuration;
   wherein an amount by which the curvable portion curves varies with an amount by which the curvable portion extends from the outer tube;
   wherein a distal end of the cannula defines a first portion of a longitudinal axis, wherein the straight portion defines a second portion of the longitudinal axis, and wherein an angle defined between the first portion of the longitudinal axis and the second portion of the longitudinal axis is variable in response to extension of the cannula from the outer tube or retraction of the cannula into the outer tube.

2. The vitreoretinal instrument of claim 1, wherein the one or more ports further comprises a tip port formed at a distal tip of the curvable portion.

3. The vitreoretinal instrument of claim 1, wherein the plurality of lateral ports are arranged in two or more rows.

4. The vitreoretinal instrument of claim 3, wherein the two or more rows are arranged symmetrically relative to a plane defined by a longitudinal axis of the curvable portion.

5. The vitreoretinal instrument of claim 3, wherein the plurality of lateral ports progressively decrease in size with increasing distance away from a distal tip of the curvable portion.

6. The vitreoretinal instrument of claim 1, wherein at least one of the plurality of lateral ports is oval in shape.

7. The vitreoretinal instrument of claim 1, wherein the second radius is larger than the first radius, and wherein the second curved portion is located closer to a distal tip of the curvable portion than the first curved portion.

8. The vitreoretinal instrument of claim 1, wherein the first radius and the second radius are adjustable.

9. The vitreoretinal instrument of claim 1, wherein the curvable portion comprises at least one elastic material selected from a group consisting of a thermoplastic elastomer and a shape memory alloy.

10. The vitreoretinal instrument of claim 1, further comprising a vacuum source and a tubing fluidly coupled to the vacuum source and the one or more ports, wherein the tubing extends into the handle, and wherein the handle comprises a compression valve moveable between a first position in which the tubing is placed into an open configuration and a second position in which the tubing is placed into a closed configuration.

11. The vitreoretinal instrument of claim 1, wherein the curvature of the first curved portion adjusts the angle of the distal end of the curvable portion to be within a range of approximately 88 degrees to 92 degrees and wherein the second radius is within a range of about 8 millimeters (mm) to 10 mm.

12. The vitreoretinal instrument of claim 1, further comprising an optical fiber extending through a lumen of the cannula to provide intraocular illumination through the cannula.

13. The vitreoretinal instrument of claim 12, wherein the cannula comprises a light transmitting window and the optical fiber is operatively coupled to the light transmitting window to provide intraocular illumination through the window.

14. A method for operating a vitreoretinal instrument in order to remove subretinal fluid, the method comprising:
providing the vitreoretinal instrument, the vitreoretinal instrument comprising:
a handle; and
a cannula coupled to the handle, the handle comprising:
a straight portion;
a curvable portion configurable between a straight configuration and a curved configuration, the curvable portion comprising an outer curvature and an inner curvature when the curvable portion is configured in the curved configuration, the curved configuration comprising:
a first curved portion having a curvature defined by a first radius, wherein the curvature of the first curved portion angles a distal end of the curvable portion along a choroid; and
a second curved portion having a curvature defined by a second radius, wherein the second radius is different from the first radius and wherein the curvature of the second curved portion conforms to a shape of the choroid; and
one or more ports formed in the curvable portion;
positioning the vitreoretinal instrument in a subretinal space of an eye such that the curvable portion is at least partially in the subretinal space; and
aspirating fluid from the subretinal space through at least the one or more ports;
wherein the one or more ports comprises a plurality of lateral ports formed only along a length of a portion of the curvable portion and only along the outer curvature of the curved configuration;
wherein the cannula is extendable and retractable within an outer tube of the vitreoretinal instrument, wherein the entire outer tube is straight, and wherein a shape of the curvable portion is variable between the curved configuration as the cannula is extended from the outer tube and the straight configuration as the cannula is retracted into the outer tube;
wherein the method further comprises extending and retracting the cannula from the outer tube through a mechanism on the handle;
wherein an amount by which the curvable portion curves varies with an amount by which the curvable portion extends from the outer tube; and
wherein a distal end of the cannula defines a first portion of a longitudinal axis, wherein the straight portion defines a second portion of the longitudinal axis, and wherein an angle defined between the first portion of the longitudinal axis and the second portion of the longitudinal axis is variable in response to extension of the cannula from the outer tube or retraction of the cannula into the outer tube.

15. The method of claim 14, wherein the plurality of lateral ports are arranged in two or more rows and wherein the lateral ports progressively decrease in size with increasing distance from the tip port.

16. The method of claim 14 wherein the one or more ports further comprises a tip port formed in a distal tip of the curvable portion.

17. The method of claim 14, wherein the curvature of the first curved portion adjusts the angle of the distal end of the curvable portion to be within a range of approximately 88 degrees to 92 degrees and wherein the second radius is within a range of about 8 millimeters (mm) to 10 mm.

18. The method of claim 14, further comprising illuminating an intraocular space through an optical fiber extending through a lumen of the cannula to provide intraocular illumination through the cannula.

19. The method of claim 18, wherein the cannula comprises a light transmitting window and the optical fiber is operatively coupled to the light transmitting window to provide intraocular illumination through the window.

* * * * *